United States Patent [19]

Clausen et al.

[11] Patent Number: 4,643,641
[45] Date of Patent: Feb. 17, 1987

[54] METHOD AND APPARATUS FOR STERILIZATION OF A CENTRIFUGAL PUMP

[75] Inventors: Earl W. Clausen, Wayzata; Lloyd C. Hubbard, Minnetonka, both of Minn.

[73] Assignee: MICI Limited Partnership IV, Minneapolis, Minn.

[21] Appl. No.: 648,498

[22] Filed: Sep. 10, 1984

[51] Int. Cl.[4] ............................................. F04D 29/12
[52] U.S. Cl. ................................. 415/170 A; 415/174; 415/DIG. 4
[58] Field of Search ............... 415/170 R, 170 A, 171, 415/172 R, 173 R, 174, DIG. 4; 277/96, 96.2

[56] References Cited

U.S. PATENT DOCUMENTS

| Re. 28,742 | 3/1976 | Rafferty et al. | 415/90 |
| 2,027,505 | 1/1936 | Winkler | 277/89 |
| 2,250,348 | 7/1941 | Beier | 277/96 |
| 2,276,622 | 3/1942 | Leake | 277/96.2 |
| 2,373,443 | 4/1945 | Armington | 277/96 |
| 2,403,298 | 7/1946 | Payne | 277/96 |
| 2,404,816 | 7/1946 | Snyder | 277/96 |
| 2,769,390 | 11/1956 | Heimbuch | 415/170 A |
| 3,608,088 | 9/1971 | Dorman et al. | 3/1 |
| 3,647,324 | 3/1972 | Rafferty et al. | 417/420 |
| 3,767,212 | 10/1973 | Ludwig | 277/96 |
| 3,864,055 | 2/1975 | Kletschka et al. | 415/1 |
| 3,957,389 | 5/1976 | Rafferty et al. | 415/1 |
| 3,970,408 | 7/1976 | Rafferty et al. | 415/60 |
| 4,037,984 | 7/1977 | Rafferty et al. | 415/60 |
| 4,135,253 | 1/1979 | Reich et al. | 3/1 |
| 4,402,515 | 9/1983 | Malott | 277/24 |

Primary Examiner—Everette A. Powell, Jr.
Attorney, Agent, or Firm—Kinney & Lange

[57] ABSTRACT

A centrifugal blood pump has a face seal between a pump housing wall and a hub of an impeller which provides upon assembly a gas permeable seal at a seal interface surrounding a shaft defining the rotational axis of the impeller. This seal separates a blood pumping chamber from a separate chamber housing lubricants and bearings for impeller rotation. Prior to rotation of the impeller, the blood pump is sterilized by exposure to ethylene oxide gas which passes through the gas permeable seal interface to also sterilize the interior of the bearing chamber in the pump. Upon rotation of the impeller, the seal interface, which is perpendicular to the axis, is converted to a gas and liquid impermeable seal.

23 Claims, 10 Drawing Figures

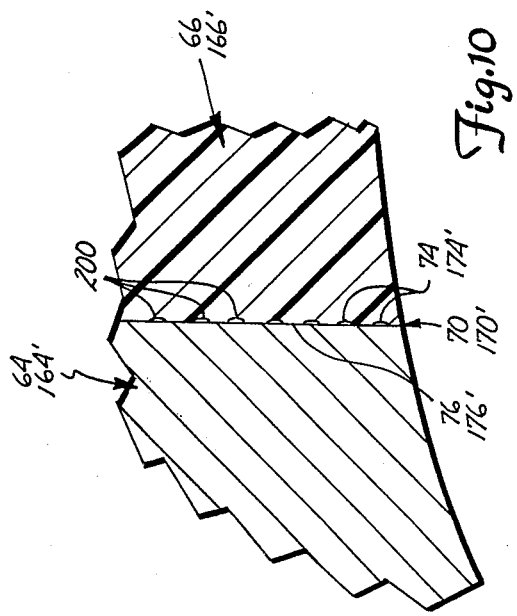
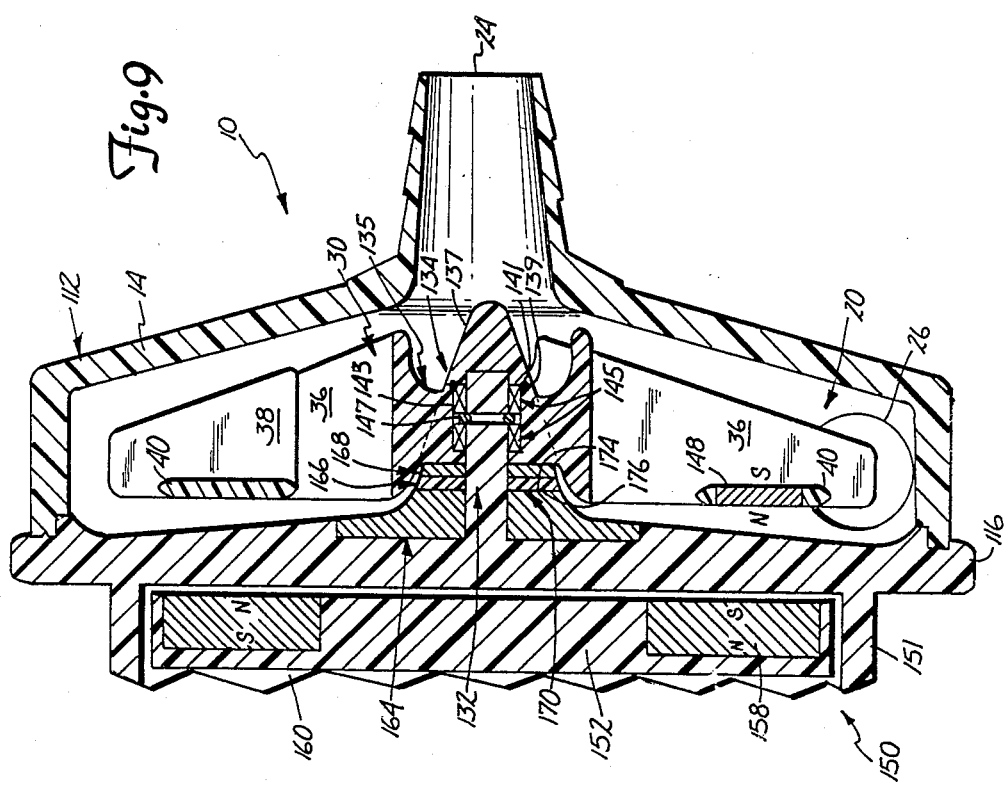

METHOD AND APPARATUS FOR STERILIZATION OF A CENTRIFUGAL PUMP

REFERENCE TO COPENDING APPLICATIONS

Reference is made to our copending applications filed on July 9, 1984 entitled "Centrifugal Blood Pump with Impeller" (Ser. No. 628,756 now U.S. Pat. No. 4,589,822), "Centrifugal Blood Pump with Tapered Shaft Seal" (Ser. No. 628,727 now U.S. Pat. No. 4,606,698), and "Centrifugal Blood Pump with Backflow Detection" (Ser. No. 628,757).

BACKGROUND OF THE INVENTION

1. Field of the Invention

The present invention is related to fluid impermeable seals, and specifically to an apparatus and method for creating such seals in a centrifugal blood pump after sterilization thereof.

2. Description of the Prior Art

Centrifugal pumps have been used for many years to pump a wide variety of different fluid materials. In general, a centrifugal pump includes a pumping chamber with an inlet aligned with a rotational axis of the pump, an outlet adjacent the periphery of the pumping chamber, and an impeller mounted within the pumping chamber for rotation about the axis. The impeller in such pumps can be mounted on a drive shaft which extends outside the pumping chamber to a rotational drive source or the shaft can be mounted within the pumping chamber as a spindle about which the impeller rotates (rotatably driven by means other than the rotation of the shaft, such as a magnetic drive arrangement). In any case, as the impeller is rotated, it imparts centrifugal force and velocity to the fluid, thus pumping the fluid from the pump inlet to the pump outlet.

In recent years, centrifugal pumps have been used extensively for pumping blood during open heart surgery. Examples of centrifugal blood pumps are shown in the following U.S. Pat. Nos.: Rafferty et al Re. 28,742; Dorman et al 3,608,088; Rafferty et al 3,647,324; Kletschka et al 3,864,055; Rafferty et al 3,957,389; Rafferty et al 3,970,408; Rafferty et al 4,037,984; and Reich et al 4,135,253.

The pumping of blood requires great care to avoid any damage to the red corpuscles, or any of the other constituents of blood. Any practical blood pump useful as part of heart/lung bypass equipment during open heart surgery must deliver the requisite flow volumes under pressure, without damaging the blood being pumped.

In a centrifugal pump, and in particular in a centrifugal pump for pumping liquids such as blood, a fluid tight seal between the drive shaft and the housing is an important factor in terms of both performance of the pump and non-contamination of the blood being pumped. If the seal is not complete (i.e., permeable), lubricants for the rotating parts of the pump or other contaminants might seep into the blood, or vice versa, which are undesirable situations for a number of reasons, including medically-related concerns and potentially decreased pump life.

Disposable blood pumps, because of their use in surgery, must be supplied sterile and ready for use. Typically, the most common method of sterilizing such a pump is for the unit to be sealed in a gas permeable bag and then exposed to ethylene oxide gas (ETO). Prior art disposable centrifugal blood pumps generally have two separate chambers—a chamber which will contain the blood being pumped and a chamber which contains the bearings for the rotating portions of the centrifugal blood pump. Blood is excluded from the bearing chamber by a shaft seal. Although the bearing chamber should never have blood contact, it must be sterilized to avoid the possibility of contamination due to a seal leak.

Prior art centifugal blood pumps have been made with a lip seal between the pumping and bearing chambers and were assembled with a short length of nylon monofilament line between the lip seal and the shaft before the blood pump assembly is sealed in its gas permeable bag. Thus, when the pump is exposed to ethylene oxide gas, the gas can enter and sterilize the bearing chamber through the gap caused in the seal by the presence of the nylon line. One end of the nylon line extends out the outlet of the blood chamber so that it can be grasped through the sterile bag and pulled out of the pump (after ETO exposure) before the pump is boxed for shipment. Of course, each bag then contains not only a sterile pump, but a short length of nylon line.

There are two principal disadvantages to the above described method of pump sterilization. First, extra packaging and handling is required. Second, the nylon bearing chamber line sterilization method precludes prepackaging of centrifugal blood pumps in sterile tubing packs preferred for use by perfusionists in their heart lung consoles. The pre-packaging of such devices such as filters into a pre-connected set-up before sterilization is now in common use because of its convenience and because it minimizes the danger of contamination by bacteria.

In some prior art centrifugal blood pumps, the bearing chamber has a separate inlet in its housing for introduction of fluid lubricant and later the introduction of ETO gas during sterilization. Of course, this arrangement presents the added complexity of requiring this inlet to be sealed after sterilization and the use of fluid bearings increases the cost of such blood pumps. If the bearing chamber were left unsealed, a patient could be exposed to a potentially fatal infusion of air into the blood stream should the seal between the blood pumping chamber and the bearing chamber fail during use.

SUMMARY OF THE INVENTION

The present invention relates to the method and apparatus for converting a gas permeable seal into a gas impermeable seal and specifically for use with respect to centrifugal pumps. In one embodiment, a smooth planar first seal face is fixed about an opening through a wall. A rotatable member covers the opening and has an uneven generally planar second seal face which abuts the first seal face but fails to create a gas impermeable seal about the opening because of the unevenness of the second seal face. The rotatable member and second seal face thereon are rotated with respect to the first seal face to burnish the unevenness on the second seal face, make the second seal face smooth and create a gas impermeable seal between the first and second seal faces about the opening.

In another embodiment, the seal is created about a shaft which defines a rotational axis and the annular smooth first seal face is generally perpendicular to the rotational axis and fixed around the shaft. The rotatable member is a hub which covers a portion of the shaft and has the uneven generally planar second seal face mounted with respect thereto. The hub is rotated with respect to the first seal face to burnish the unevenness of the second seal face, make the second seal face smooth and create a gas impermeable seal between the first and second seal faces.

Preferably, the seals created as described above separate two chambers and prior to rotating the rotatable member or hub, a desired gas is introduced into one of the chambers so that the gas passes through the gas permeable seal and into the other chamber. For medical sterilization purposes, the desired gas is ethylene oxide.

In a centrifugal blood pump, the seal described above creates a seal interface between a blood pumping chamber and a second chamber containing rotational drive or lubricant elements for the pumps impeller and other rotating components. The seal preferably includes a nonrotatable seal stator and a rotatable seal rotor. The seal stator has a first seal face which engages a second seal face on the seal rotor at the seal interface. The first seal face of the seal stator is smooth and the second seal face of the seal rotor is uneven so that when the first and second seal faces are urged together, tiny pathways for gas travel are created around the seal interface because of the unevenness of the second seal face. The seal rotor is preferably formed from materials softer than the material forming the seal stator. Prior to rotating the seal rotor with respect to the seal stator, ethylene oxide gas is introduced into the blood pumping chamber. The gas passes through the tiny pathways at the seal interface and into the second chamber of the pump. Thus, all components of the pump are sterilized. Rotation of the seal rotor with respect to the seal stator burnishes the second seal face smooth and creates a gas and liquid impermeable seal at the seal interface.

BRIEF DESCRIPTION OF THE DRAWINGS

FIG. 9 is a sectional view of another embodiment of the centrifugal pump of the present invention, along a view similar to that of FIG. 3.

FIG. 10 is an enlarged partial sectional view of a portion of the seal interface prior to operation of the centrifugal pump.

DETAILED DESCRIPTION OF THE PREFERRED EMBODIMENTS

Figure 1:
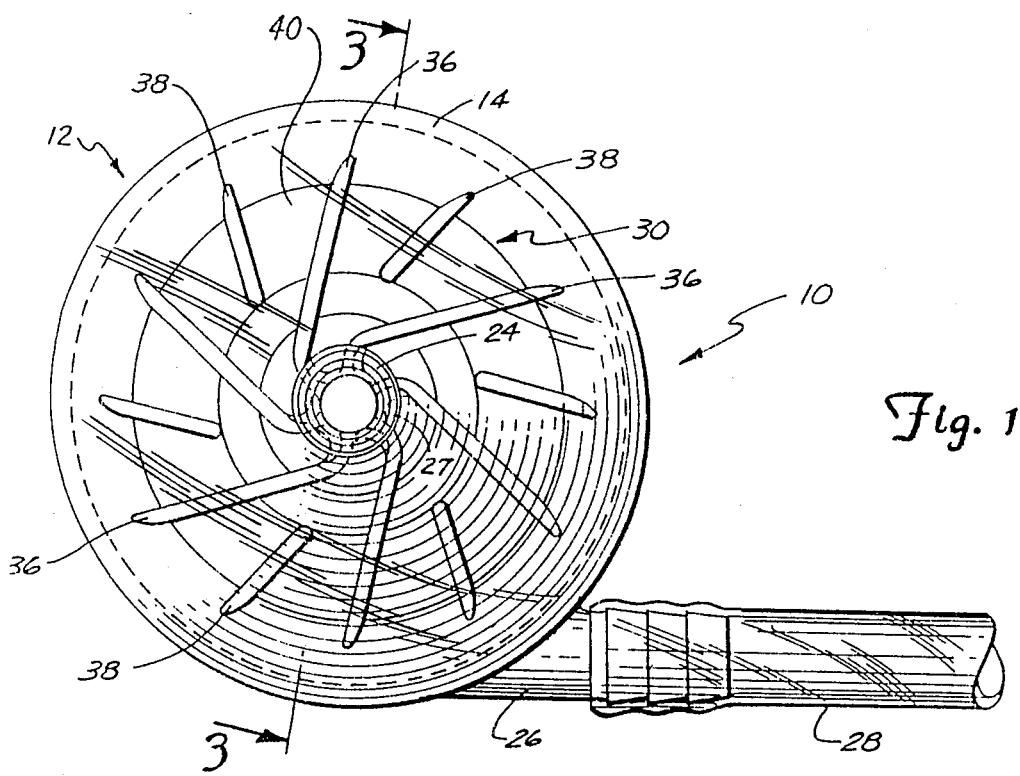
FIG. 1 is a front view of the centrifugal pump of the present invention.
Figure 2:
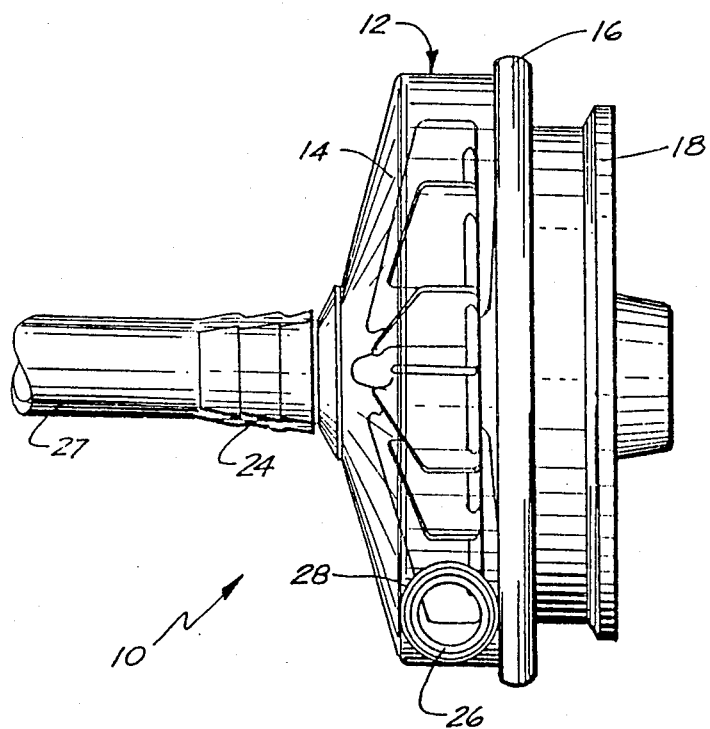
FIG. 2 is a side view of the centrifugal pump.

In the FIGS. 1–8, centrifugal pump 10 of the present invention includes a three-part housing 12 formed by front housing section 14, center wall housing section 16, and rear housing section 18. Front and center sections 14 and 16 are sealed to define pumping chamber 20. Center and rear sections 16 and 18 are sealed to define rotor chamber 22.

Front housing section 14 (which is preferably transparent so that operation of the pump can be visually monitored) includes axially aligned pump inlet 24 and tangential pump outlet 26. Blood or other biological fluid is received at inlet 24 from inlet tubing 27 and is pumped to outlet 26 and outlet tubing 28 by rotation of impeller 30 within pumping chamber 20.

Figure 3:
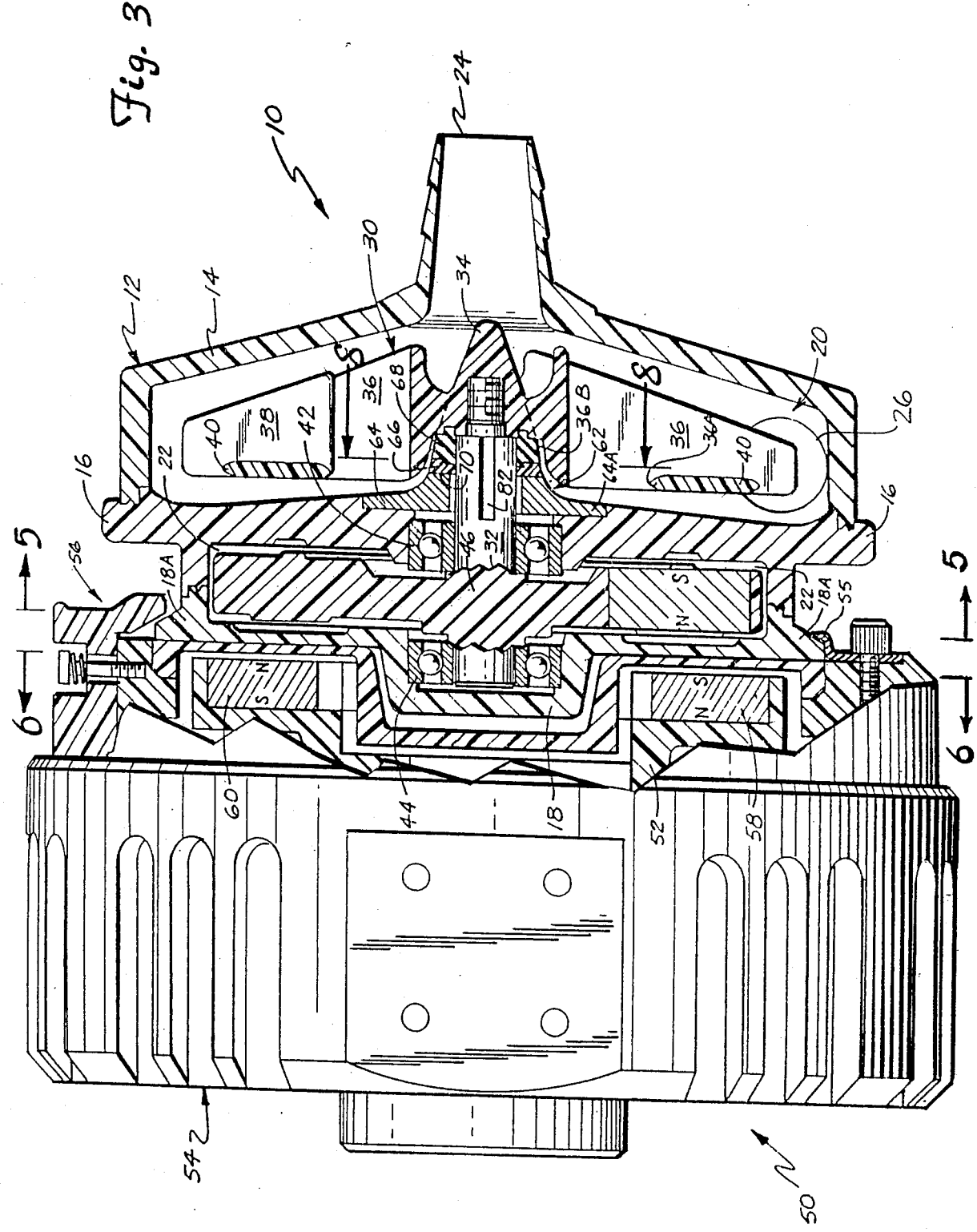
FIG. 3 is a sectional view of the centrifugal pump along section 3—3 of FIG. 1.
Figure 4:
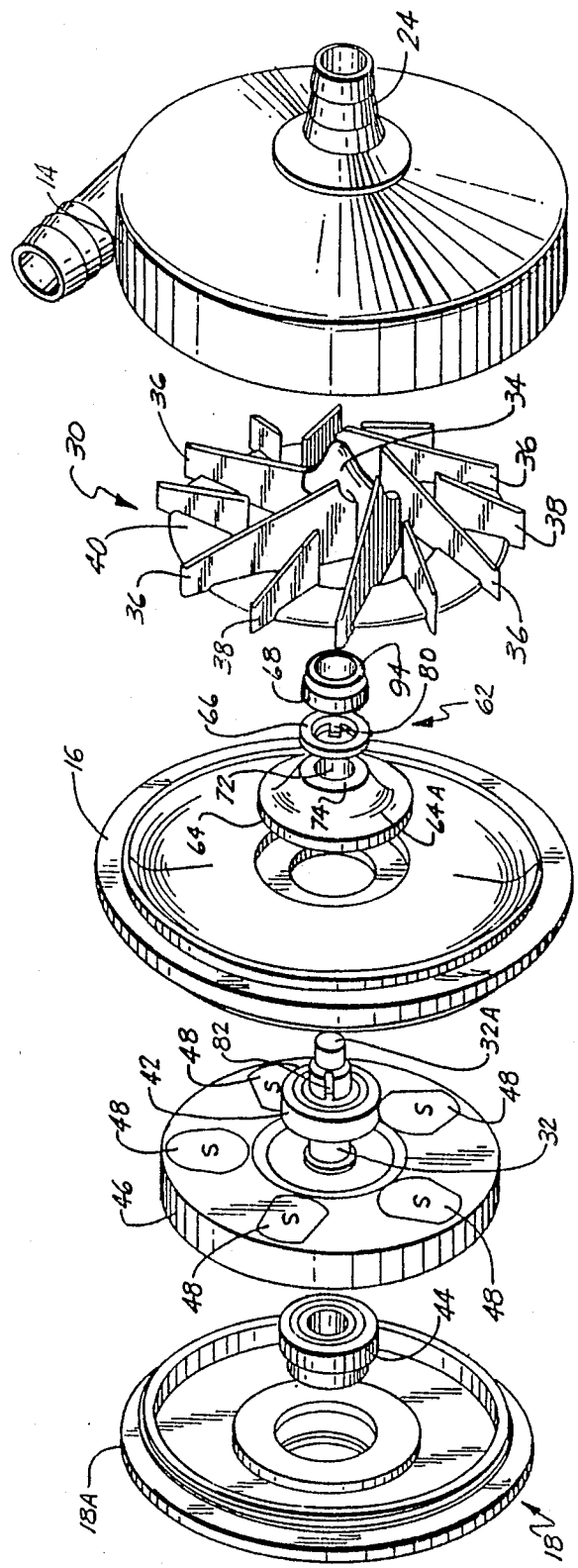
FIG. 4 is an exploded perspective view of the centrifugal pump.
Figure 7:
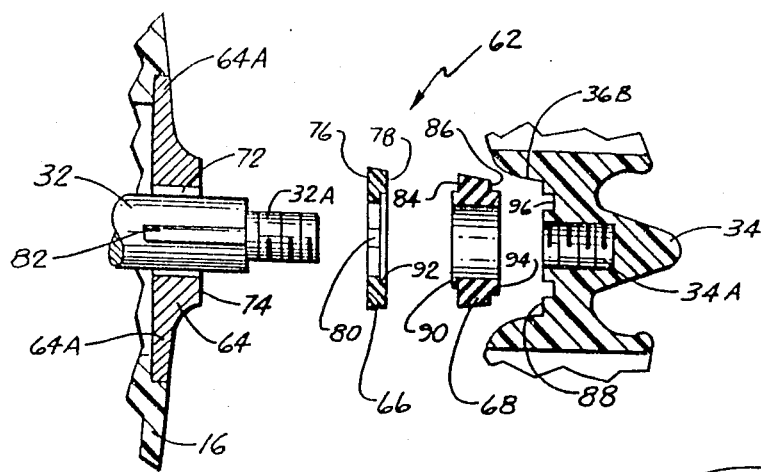
FIG. 7 is an exploded view, partially in section, of the tapered shaft seal of the centrifugal pump.
Figure 5:
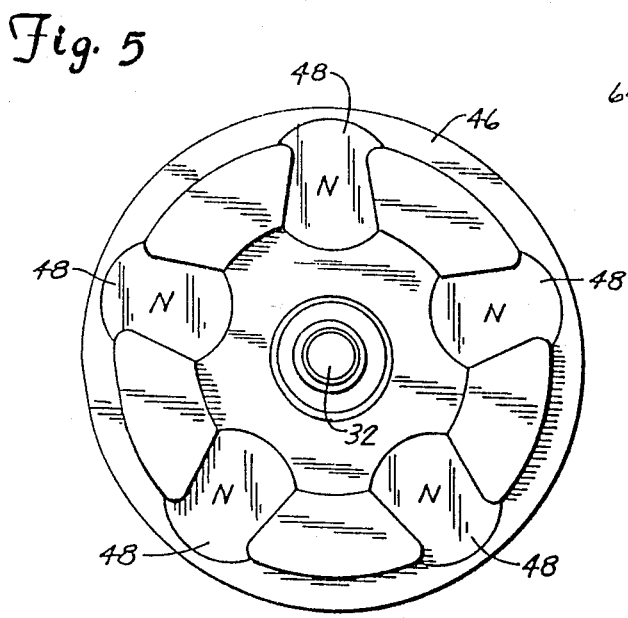
FIG. 5 is a view of the rotor along view 5—5 of FIG. 3.
Figure 8:
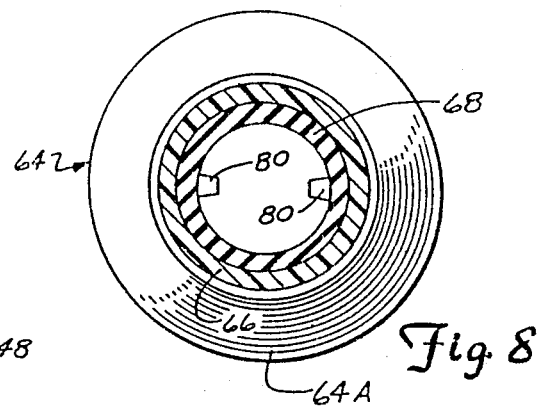
FIG. 8 is a sectional view of the shaft seal along section 8—8 of FIG. 3.

In the embodiment shown in FIG. 3, impeller 30 is mounted on a threaded outer end 32A of shaft 32, and is rotated about an axis defined by shaft 32. Impeller 30 includes a conical shaped impeller hub 34 (with internal threads 34A for engaging threaded outer end 32A), a plurality of long blades 36, a plurality of short blades 38, and circular flange 40.

Long blades 36 are attached at their inner ends to impeller hub 34. Flange 40 is attached to and is supported by the lower edges of long blades 36. Short blades 38 are supported by flange 40. In the embodiments shown in the Figures, long and short blades 36 and 38 are alternately spaced about the circumference of impeller 30.

Large diameter impellers require a greater number of blades in order to achieve pumping efficiency. By use of short blades 38 supported by flange 40, impeller 30 achieves pumping efficiency while retaining a small hub diameter, since only long blades 36 are attached to hub 34.

Shaft 32 is mounted for rotation by a pair of axially aligned ball bearings 42 and 44. Ball bearing 42 is press fitted into center wall section 16, while ball bearing 44 is press fitted into rear housing section 18.

Rotor 46 is connected to shaft 32, so that as rotor 46 rotates within rotor chamber 22, shaft 32 and impeller 30 are rotated. In the embodiments shown in the Figures, pump 10 is a magnetically driven pump. Rotor 46 carries a plurality of small ceramic disk magnets 48. Each magnet 48 has the same pole orientation (which in the particular embodiment shown) has the north (N) pole closest to drive console 50. Magnets 48 are equally spaced around the circumference of rotor 46 and, in the particular embodiment shown in FIG. 3, five magnets 48 spaced at 72° intervals from one another are carried by rotor 46.

Drive console 50 includes drive plate 52 which is rotated by motor 54 about an axis which is aligned with the axis of shaft 32. Clip 55 and spring-loaded latch 56 engage flange 18A of rear housing section 18 to hold pump housing 12 in position adjacent drive console 50. Pump housing 12 can be quickly removed from engagement with drive console 50 by lifting latch 56.

Figure 6:
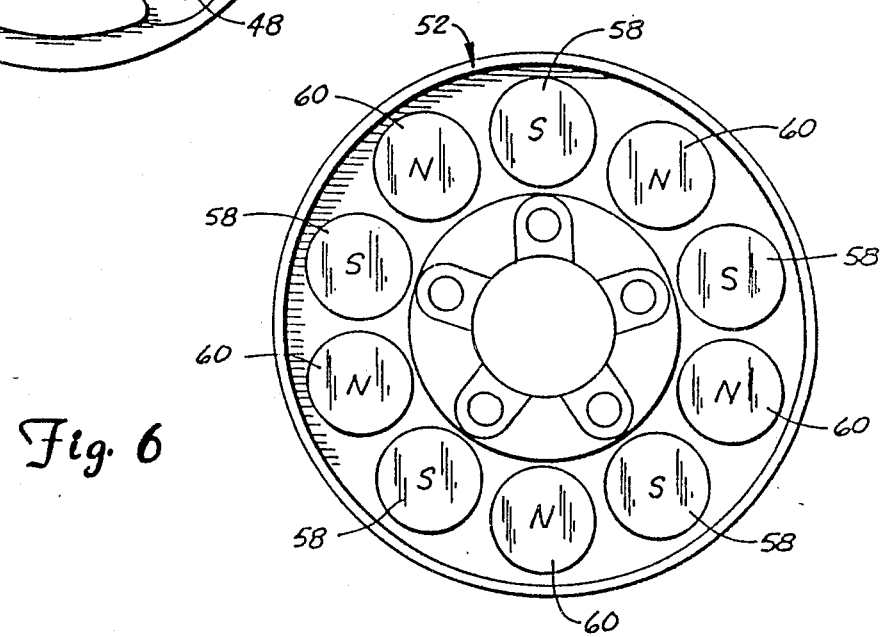
FIG. 6 is a view of the drive plate along view 6—6 of FIG. 3.

Drive plate 52 carries five equally spaced south (S) pole magnets 58 and five equally spaced north (N) pole magnets 60. Magnets 58 and 60 are arranged alternately (as shown in FIG. 6). This gives both attractive and repelling force to magnets 48 carried by rotor 46. This magnetic drive allows the use of small, discrete magnets in pump 10, rather than a single large magnet with mulitple poles. This provides a significant cost reduction which is of particular advantage since pump housing 12, when used for pumping blood or other biological fluids, must be disposed of after a single use.

In the present invention, leakage of fluid from pumping chamber 20 into rotor chamber 22 is prevented by a tapered shaft seal 62 formed by seal stator 64, seal rotor 66, and resilient elastomer spring 68. Tapered seal 62 is tapered to conform to the taper of impeller hub 34 so that an air bubble (which seeks the smallest shaft diameter within pumping chamber 20) will not insulate the seal interface edges from fluid flow. Tapered seal 62 provides a seal interface 70 between seal stator 64 and seal rotor 66 which is generally perpendicular to the axis of shaft 32 and which is located at an intermediate position between wall 16 and hub 34. The location of the seal interface 70 is in a high fluid flow area, which increases cooling effects and improves dissipation of heat caused by friction at seal interface 70.

In the embodiment of the present invention shown in FIG. 3, seal stator 64 is fixed to center wall section 16 and formed from a high thermal conductivity material (preferably nickel-plated aluminum). Seal stator 64 has a central passage 72 which is axially aligned with shaft 32 and is of sufficient diameter so that shaft 32 does not contact seal stator 64. Front face 74 of seal stator 64 defines the location of seal interface 70 and is preferably generally perpendicular to the axis of shaft 32.

Seal stator 64 has a flange 64 at its rear end which extends outward in a radial direction and generally conforms to the surface of wall section 16 at the rear end of pumping chamber 20. Flange 64B provides a large surface area for seal stator 64, thus increasing the ability of seal stator 64 to transfer heat generated at seal interface 70.

Seal rotor 66 is positioned on shaft 32 adjacent to seal stator 64. Rear seal face 76 of seal rotor 66 engages front seal face 74 of seal stator 64 to provide seal interface 70. Front face 78 of seal rotor 66 faces and is engaged by spring 68. Seal rotor 66 has a pair of inwardly projecting keys 80 which engage axially extending keyways 82 on shaft 32 so that seal rotor 66 can move in the axial direction and yet rotates with shaft 32. Preferably, seal rotor 66 is a low friction polymer material such as nylon.

Spring 68 is an elastomer (such as silicone rubber) ring which is mounted coaxially on shaft 32 between impeller hub 34 and seal rotor 66. Rear face 84 of spring 68 engages front face 78 of seal rotor 66, and front face 86 of spring 68 engages rear face 88 of hub 34. Elastomer spring 68 is maintained under compression by hub 34, which is threaded on outer end 32A of shaft 32, so that it urges seal rotor 66 in an axial direction into engagement with seal stator 64. Sprng 68 preferably has an annular rib 90 which is positioned in annular groove 92 in front face 78 of seal rotor 66 and has an annular rib 94 which is positioned in annular groove 96 in the rear face 98 of hub 34. Ribs 90 and 94 help to maintain an axial alignment of spring 68 so that an essentially uniform axial force is applied to seal rotor 66. In another embodiment (not shown), the resilient elastomer spring is positioned between the seal stator and wall section with which it is mounted (rather than between the seal rotor and hub) and the seal rotor is fixed to the hub to effectuate the sealing of the pumping chamber about the shaft.

To increase fluid flow in the area of seal interface 70, each of the long blades 36 of impeller 30 has a lower edge 36A which is below the lower edge of impeller hub 34. Each long blade 36 has an inner edge 36B which extends from lower edge 36A to impeller hub 34, and which is closely spaced and generally parallel to the outer surface of tapered seal 62.

An alternative embodiment of the centrifugal pump 10 is shown in FIG. 9. In this embodiment, those elements of the centrifugal pump 10 which are the same as those described above are provided with the same reference numbers. New elements or elements that differ from similar elements shown in the embodiment illustrated in FIGS. 1–8 are provided with reference numbers one hundred numbers higher than the prior reference numbers.

In the embodiment shown in FIG. 9, a two-part housing 112 is partially defined by a center wall housing section 116 which has a shaft 132 affixed in the center thereof. Thus, the shaft 132 thus does not rotate when the impeller 30 is rotated. The impeller 30 includes a conically shaped impeller hub portion 134 which is formed from two sections: a first hub section 135 which provides support for the inner ends of the long blades 36 of the impeller 30 and a conical hub cap section 137 which is fixedly mounted on the first section 135 of the hub 134 as at 139. The hub sections can be affixed together by any suitable means such as threaded engagement, adhesives, etc. Sealing means, such as resilient seal ring 141 is provided between the first section 135 and cap section 137 of the hub 134 to further seal the joint between those hub sections in a liquid and gas impermeable manner. When so connected, the hub sections define an inner bearing chamber 143 in the interior of the hub adjacent the shaft 132. The hub 134 is mounted for rotation about the shaft 132 by axially aligned bearing means 145 mounted in the bearing chamber 143. Suitable hub retention means, such as a spring clip 147 secured in an annular groove about shaft 132 retain hub 134 in position axially on shaft 132.

Flange 40 carries a plurality of small magnets 148. Each magnet 148 has the same pole orientation (which in the particular embodiment shown has the north (N) pole closest to center wall section 116). Magnets 148 are equally spaced about the circumference of flange 40 in a manner similarly as described above with respect to the embodiment shown in FIGS. 3 and 5 (five magnets 148 spaced at 72° intervals (center-to-center) from one another about flange 40).

A drive console 150 having a console housing 151 is selectively securable to the two-part housing 112 along center wall housing section 116 as shown. Suitable means (not shown) are provided for securing console housing 151 of drive console 150 to housing 112. Drive console 150 includes a drive plate 152 which is rotated by a motor (not shown) about an axis which is aligned with the axis of shaft 132. Drive plate 152 carries five equally spaced south (S) pole magnets 158 and five equally spaced north (N) pole magnets 160. Magnets 158 and 160 are arranged alternatively to give both attractive and repelling force to magnets 148 carried by flange 40.

In the embodiment of the present invention shown in FIG. 9, leakage of fluid from pumping chamber 20 into inner bearing chamber 143 is prevented by a tapered shaft seal 162 formed by seal stator 164, seal rotor 166, and resilient elastomer spring 168. Tapered seal 162 provides a seal interface 170 between seal stator 164 and seal rotor 166 which is generally perpendicular to the axis of shaft 132 and which is located at an intermediate position between center wall housing section 116 and hub 134.

In the embodiment of the present invention shown in FIG. 9, seal stator 164 is fixed to center wall section 116, and is formed from a high thermal conductivity metal material (such as nickel-plated aluminum or anodized aluminum). Front seal face 174 of seal stator 164 defines the location of seal interface 170 and is generally perpendicular to the axis of shaft 132.

Seal rotor 166 is positioned on shaft 132 adjacent to seal stator 164. Rear seal face 176 of seal stator 166 engages front seal face 174 of seal stator 164 to provide seal interface 170. Spring 168 is positioned about shaft 132 between seal rotor 166 and hub 134 as shown. The first section 135 of hub 134, spring 168 and seal rotor 166 are suitably coupled (by e.g., keyways, adhesives, friction fit, etc.) to rotate together about shaft 132. Seal rotor 166, though coupled for rotation with spring 168, is movable axially with respct to shaft 132 and is urged toward seal stator 164 by spring 168. Preferably, seal rotor 166 is a low-friction polymer material such as nylon.

Elastomer spring 168 is maintained under compression by hub 134 which is retained in axial position on shaft 132 by spring clip 147 as described above. Of course, other suitable means for maintaining the axial position of hub 134 on shaft 132 may be used. Spring 168 can also be provided with annular ribs (such as ribs 90 described in the embodiment shown in FIGS. 1-8) which cooperate with annular grooves in seal rotor 166 and first section 135 of hub 134 to help maintain an axial alignment of spring 168 so that an essentially uniform axial force is applied to seal rotor 166. Other hub configurations and arrangements for defining bearing chamber 143 are also contemplated.

In operation, the seal in a centrifugal blood pump between the pumping and bearing chambers of the pump must be liquid and gas impermeable to prevent contaminants (e.g., lubricants) in the bearing chamber from entering the blood pumping chamber. In the present invention, the seal interface between the two chambers is a planar face seal which is transverse to the axis of pump impeller rotation.

Preferably, front seal face 74, 174 of seal stator 64, 164 is a smooth planar face. Rear seal face 76, 176 of seal rotor 66, 166 is a generally uneven planar face. The unevenness of rear seal face 76, 176 of seal rotor 66, 166 can be created when seal rotor 66, 166 is created (molded) or can be later added prior to assembly of the pump by abrasion or scoring of rear seal face 76, 176 of seal rotor 66, 166.

When the seal rotor, seal stator and other pump components are assembled as generally illustrated in FIGS. 3 and 9, the unevenness on the rear seal face of the seal rotor abuts the smooth front seal face of the seal stator, as shown in FIG. 10. The seal interface 70, 170 created thereby is gas permeable because of the unevenness of the rear seal 76, 176. Thus, tiny pathways 200 (as shown in FIG. 10) for gas travel are created across the seal interface 70, 170. A gas permeable "seal" is thus created at the seal interface 70, 170.

To sterilize the centifugal pump, the pump is packaged in a gas permeable pouch, box or carton prior to sterilization by exposure to ethylene oxide gas. The gas enters the pumping chamber 20 and passes through pathways 200 into the other chamber in the pump (bearing chamber rotor chamber 22 in the embodiment of FIG. 3 or bearing chamber 143 in the embodiment of FIG. 9). The interior elements of the other chamber are thus exposed to the gas and sterilized and any possible leak between chambers of the centrifugal pump 10 during use will not, therefore, result in nonsterile contamination of the blood being pumped. The pathways 200 are formed to be so small that little or no liquid (which may be used in priming the pump and heart/lung system) will pass through the seal interface 70, 170 when the pump is first put into use.

The gas permeable "seal" at seal interface 70, 170 is converted into a gas impermeable seal by operation of pump 10. In the embodiment shown in FIG. 3, rotation of shaft 32 causes rotation of seal rotor 66 with respect to seal stator 64. With respect to the embodiment shown in FIG. 9, rotation of hub 134 causes rotation of seal rotor 166 with respect to seal stator 164. In either case, such rotation of the seal rotor with respect to the seal stator quickly burnishes or "polishes" the unevenness on the rear seal face of the seal rotor to make it smooth. The tiny pathways 200 are eliminated through such burnishing action in a relatively short time (less than a minute) and the seal becomes an impermeable seal at the seal interface to gas as well as liquid. As stated, the seal rotor is preferably formed from a polymer material. Frictional heat generated by the rubbing of the seal rotor against the seal stator at the seal interface during rotation of the seal rotor also assists in smoothing down the unevenness of the rear seal face of the seal rotor by softening the polymer material of the seal rotor.

With a centrifugal blood pump of the present invention, the pump can be packaged in a gas permeable pouch, box or carton prior to sterilization. After sterilization, the pumps can then be shipped to customers in the same package in which they were sterilized, as is the common practice with other such products. In addition, the pumps may be shipped in a bulk nonsterile state to manufacturers of "custom tubing packs" who then may include them in their products prior to sterilization of the completed pack, which presents a distinct advantage over the situation with respct to prior art blood pumps and the necessity for sterilization.

Although the present invention has been described with reference to preferred embodiments, workers skilled in the art will recognize that changes may be made in form and detail without departing from the spirit and scope of the invention. For example, although the particular embodiment of pump 10 shown in the Figures utilizes a synchronous magnetic drive, the shaft seal is equally applicable to pumps in which other forms of coupling (including direct coupling) between shaft 32 of pump 10 and motor 54 of console 50 are provided. In addition, the seal stator can bear the uneven seal face and be formed from a softer material than the seal rotor, which then bears the smooth seal face.

What is claimed is:

1. A method of forming a gas permeable seal about an opening through a wall and converting that seal into a gas impermeable seal after a desired gas passage through the seal, the method comprising the steps of;
    providing a first seal face fixed with respect to a wall about an opening therethrough;
    covering the opening with a rotatable member having a second seal face in abutment with the first seal face, the first and second seal faces being generally planar with one of said seal faces being smooth and the other seal face being uneven to form a gas permeable seal about the opening through the unevenness of the uneven seal face; and
    rotating the rotatable member and second seal face thereon with respect to the first seal face, after said desired gas passage, to burnish the unevennness of the uneven seal face and create a gas impermeable seal between the first and second seal faces about the opening.

2. The method of claim 1 wherein the wall separates two chambers, and further comprising the step of:
    introducing a desired gas into one of the chambers prior to rotating the member so that the gas passes through the gas permeable seal in the wall and into the other chamber.

3. The method of claim 2 wherein the desired gas is ethylene oxide.

4. A method of forming a gas permeable seal about a shaft which defines a rotational axis and converting that seal into a gas impermeable seal after a desired gas passage through the seal, the method comprising the steps of:
- providing an annular, first seal face around the shaft with the first seal face being generally perpendicular to the rotational axis and fixed with respect to the shaft;
- covering a portion of the shaft with a rotatable hub having a second seal face mounted with respect thereto and in abutment with the first seal face, the first and second seal faces being generally planar with one of said seal faces being smooth and the other seal face being uneven to form a gas permeable seal therebetween through the unevenness of the uneven seal face; and
- rotating the hub and second seal face with respect to the first seal face, after said desired gas passage, to burnish the unevenness of the uneven seal face and create a gas impermeable seal between the first and second seal faces.

5. The method of claim 4, wherein the seal is positioned between first and second separate chambers and further comprising the step of:
- introducing a desired gas into one of the chambers prior to rotating the member so that the gas passes through the gas permeable seal in the wall and into the other chamber.

6. The method of claim 4 wherein the desired gas is ethylene oxide.

7. A centrifugal pump comprising:
- a pump housing;
- wall means for dividing an interior of the pump housing into a drive chamber and a pumping chamber;
- a shaft extending in an axial direction from the drive chamber through the wall means into the pumping chamber to define a rotational axis;
- an impeller mounted with respect to the shaft for rotation about the rotational axis within the pumping chamber, the impeller having a hub;
- seal means between the wall means and the hub for providing a gas permeable seal at a seal interface surrounding the shaft between the drive chamber and the pumping chamber; and
- means for converting the seal means into a gas impermeable seal upon rotation of the shaft with respect to the pump housing.

8. The centrifugal pump of claim 7 wherein the seal interface is generally transverse to the axial direction.

9. The centrifugal pump of claim 7 wherein the seal means comprises:
- a seal stator mounted with respect to the wall means and surrounding the shaft, the seal stator defining a first seal face which is generally transverse to the axial direction and is located intermediate the wall means and the hub;
- a seal rotor positioned coaxially about the shaft between the seal stator and the hub, the seal rotor defining a second seal face which faces the first seal face and which is generally transverse to the axial direction, the seal rotor being mounted for rotation with the hub and being movable in the axial direction; and
- bias means for urging the first and second seal faces into engagement at the seal interface.

10. The centrifugal pump of claim 9 wherein the seal rotor is formed from a material softer than the material forming the seal stator.

11. The centrifugal pump of claim 9 wherein the first seal face of the seal stator is smooth and the second seal face of the seal rotor is uneven so that when the first and second seal faces are urged together prior to rotation of the shaft, pathways sufficiently large for gas travel but not liquid travel are created across the seal interface because of the unevenness of the second seal face.

12. The centrifugal pump of claim 9 wherein the seal rotor is a low friction polymer ring.

13. The centrifugal pump of claim 9 wherein the low friction polymer is a nylon material.

14. The centrifugal pump of claim 13 wherein the seal rotor is formed from a polymer material and the unevenness of the second seal face is molded thereon when the seal rotor is formed.

15. The centrifugal pump of claim 9 wherein the bias means comprises:
- a resilient ring positioned coaxially on the shaft between the hub and the seal rotor for urging the seal rotor toward the seal stator at the seal interface.

16. A centrifugal pump comprising:
- a pump housing having a pumping chamber therein;
- a shaft extending in an axial direction from a wall of the pump housing into the pumping chamber to define a rotational axis;
- an impeller for rotation about the rotation axis within the pumping chamber, the impeller having a hub;
- seal means between the wall of the pump housing and the hub for providing a gas permeable seal at a seal interface surrounding the shaft between the pumping chamber and an interior portion of the hub adjacent the shaft; and
- means for converting the seal means into a gas impermeable seal upon rotation of the hub with respect to the pump housing.

17. The centrifugal pump of claim 16 wherein the seal means comprises:
- a seal stator mounted with respect to the wall and surrounding the shaft, the seal stator defining a first seal face which is generally transverse to the axial direction and is located intermediate the wall means and the hub;
- a seal rotor positioned coaxially about the shaft between the seal stator and the hub, the seal rotor defining a second seal face which faces the first seal face and which is generally transverse to the axial direction, the seal rotor being mounted for rotation with the hub and being movable in the axial direction; and
- bias means for urging the first and second seal faces into engagement at the seal interface.

18. The centrifugal pump of claim 17 wherein the first seal face of the seal stator is smooth and the second seal face of the seal rotor is uneven so that when the first and second seal faces are urged together prior to rotation of the hub, pathways sufficiently large for gas travel but not for liquid travel are created across the seal interface because of the unevenness of the second seal face.

19. The centrifugal pump of claim 18 wherein the seal rotor is formed from a polymer material and the unevenness of the second seal face is molded thereon when the seal rotor is formed.

20. The centrifugal pump of claim 19 wherein the seal rotor is formed from a material softer than the material forming the seal stator.

21. A method of sterilizing a centrifugal pump for biological fluids, the method comprising the steps of:
- dividing an interior of a centrifugal pump into first and second chambers;
- sealing the first chamber from an exterior of the centrifugal pump except through an opening from the first chamber into the second chamber;
- providing a generally planar first seal face fixed with respect to the opening on one side thereof;
- covering the opening with a rotatable member having a generally planar second seal face in abutment with the first seal face, one of the planar seal faces being smooth and the other planar seal face being uneven relative to the smooth seal face to form a gas permeable seal about the opening; and
- exposing the pump and second chamber therein to a medical sterilization gas to contact and sterilize the pump exterior and second chamber and the first chamber through the gas permeable seal and opening into the first chamber;
- the member and second seal face thereon being rotatable with respect to the first seal face to smooth by burnishing the unevenness therebetween and create a gas impermeable seal between the first and second seal faces about the opening.

22. The method of claim 21, and further comprising the step of:
- packaging the pump in a sealed, gas permeable container prior to exposing the pump to the medical sterilization gas.

23. The method of claim 21 wherein the uneven seal face is formed from a material softer than the material forming the smooth seal face.

* * * * *